(12) United States Patent
Delalu et al.

(10) Patent No.: US 7,390,929 B2
(45) Date of Patent: Jun. 24, 2008

(54) METHOD FOR THE CONTINUOUS SYNTHESIS OF MONOALKYL-HYDRAZINES WITH A FUNCTIONALIZED ALKYL GROUP

(75) Inventors: Henri Delalu, Lyons (FR); Cécile Colas-Duriche, Talence (FR); Jacques Berthet, Lyons (FR); Philippe Leurent, Toulouse (FR)

(73) Assignees: Isochem, Paris (FR); Centre National de la Recherche Scientifique (CNRS), Paris (FR); Universite Claude Bernard Lyon 1, Villeurbanne (FR)

( * ) Notice: Subject to any disclaimer, the term of this patent is extended or adjusted under 35 U.S.C. 154(b) by 76 days.

(21) Appl. No.: 10/583,285

(22) PCT Filed: Dec. 17, 2004

(86) PCT No.: PCT/FR2004/003286

§ 371 (c)(1),
(2), (4) Date: Jun. 16, 2006

(87) PCT Pub. No.: WO2005/058801

PCT Pub. Date: Jun. 30, 2005

(65) Prior Publication Data

US 2007/0185351 A1    Aug. 9, 2007

(30) Foreign Application Priority Data

Dec. 17, 2003   (FR)   ................................. 03 14796

(51) Int. Cl.
*C07C 241/02*   (2006.01)

(52) U.S. Cl. ...................................... 564/466; 564/314

(58) Field of Classification Search ................. 564/466
See application file for complete search history.

(56) References Cited

U.S. PATENT DOCUMENTS 5,101,040 A    3/1992   Cohen

FOREIGN PATENT DOCUMENTS

| EP | 0 277 267 A1 | 8/1988 |
| FR | 2 651 776 A1 | 3/1991 |
| GB | 1095040 | 12/1967 |

OTHER PUBLICATIONS

Audrieth et al., Journal of the American Chemical Society, 1954, vol. 76, p. 4869-4871.*
Diamond et al., "Preparation of N-Substituted Hydrazines from Amines and Chloramine," *J. Am. Chem. Soc.*, 1955, vol. 77, p. 3131.
International Search Report dated Apr. 29, 2005 for PCT/FR2004/003286.
International Search Report dated Apr. 26, 2005 for PCT/FR2004/003288.
Sergeeva et al., "Synthesis and Properties of Allylhydrazines" *Zhurnal Organicheskoi Khimii*, 1966, pp. 983-988, vol. 3, No. 6, Leningrad State University.

* cited by examiner

*Primary Examiner*—Brian J Davis
(74) *Attorney, Agent, or Firm*—Alston & Bird LLP

(57) ABSTRACT

The invention relates to a method for the continuous synthesis of monoalkyl-hydrazines with a functionalized alkyl group. The inventive method is characterized in that it comprises a step consisting in demixing a solution containing the synthesized monoalkyl-hydrazine, by reacting an anhydrous amine with monochloramine, in an organic phase and an aqueous phase with the addition of anhydrous sodium hydroxide. The invention can be used to obtain perfect selectivity in relation to monoalkyl-hydrazine without the presence of the di- and tri-substituted forms thereof. According to the invention, the staffing amine which has not reacted is collected and reused directly without any additional treatment.

16 Claims, 1 Drawing Sheet

METHOD FOR THE CONTINUOUS SYNTHESIS OF MONOALKYL-HYDRAZINES WITH A FUNCTIONALIZED ALKYL GROUP

FIELD OF THE INVENTION

This application is a 371 of PCT/FR04/03286 filed Dec. 17, 2004 has been inserted.

The present invention relates to a method for the continuous synthesis of monoalkylhydrazines with a functionalized alkyl group.

BACKGROUND

Within the context of the present invention, "monoalkylhydrazine" is understood to mean any hydrazine of formula $NH_2$—NH—R in which R represents a functionalized alkyl group, that is to say, comprising at least one function chosen from the group consisting of a carbon-carbon (the case of allylhydrazine) or carbon-nitrogen unsaturation, a hydroxyl group (the case of 2-hydroxyethylhydrazine), an alkoxy group (the case of 2-methoxyethylhydrazine) or phenoxy group (the case of Ph—O—$CH_2$—$CH_2$—NH—$NH_2$), a carboxylic acid group, a tertiary amine function (the case of $(Me)_2N$—$CH_2$—$CH_2$—NH—$NH_2$) or a phenyl group (the case of Ph-$CH_2$—NH—$NH_2$).

The monoalkylhydrazines, in particular allylhydrazine, are compounds frequently used as intermediates in the manufacture of medicines.

At present, the only methods of synthesis described in the scientific literature call upon hydrazine hydrate ($N_2H_4$) and the nitrosamines. In the particular case of the synthesis of allylhydrazine, the first method consists of gradually adding 1.28 moles of allyl bromide to 8.96 moles of hydrazine monohydrate, which corresponds to a molar ratio of 7. During the addition, the temperature must be maintained below 40° C. The reaction mixture is then heated under reflux at 70° C. for one hour. After extraction with ether and distillation, a mixture consisting of 57% monoallylhydrazine ($CH_2$=$CHCH_2NHNH_2$), 11% diallylhydrazine (($CH_2$=CHCH2)$_2$NNH2) and triallylhydrazine is obtained. The implementation of a higher ratio decreases the quantity of the monoallylhydrazine to the benefit of the diallylhydrazine (34.6% yield in ($CH_2$=$CHCH_2$)$_2$$NNH_2$). The difficulties of allylation are at the level of the non-selectivity and the separation of the allylhydrazine in mono-, di- and tri-allylhydrazine/water/$N_2H_4$ mixtures (Loffe B. V et al., Zh. Org. Khim (1967) 3(6), 938-8). A series of patents (JP 93-256100; JP 93-261194; JP 7118218; JP 7112963) have been filed which call upon various methods to yield a compound of high purity.

A second method for the synthesis of allylhydrazine consists of a low-temperature (5° C.) nitrosation of allylhydrazine followed by a chemical hydrogenation ($LiAlH_4$) of the nitrosated derivative (1-nitrosoallylamine) in an etherated medium. The yield of the reaction does not exceed 42%. However, the product arising from the first step must be handled with much precaution because of its toxicity (it is a highly carcinogenic compound), which poses problems for its industrial production. Moreover, the use of $LiAlH_4$ requires the absence of trace amounts of water, watertight reactors and anhydrous solvents (diethyl ether), the effect of which is to increase the risks of igniting the reaction mixture.

Moreover, it is recognized that the so-called "Raschig" reaction can be called upon for the preparation of the various hydrazines, which consists of synthesizing the monochloramine by the reaction of ammonia with a sodium hypochlorite solution and reacting the monochloramine thus formed with an amine to obtain the corresponding hydrazine. This method is rather difficult to implement because it requires two distinct-steps, the first carried out at a low temperature for the synthesis of the monochloramine and the second carried out at a high temperature, in which the synthesis of the hydrazine is carried out. In addition, the monochloramine must be in the presence of a sufficient excess of amine in the intermediate solutions so as to avoid secondary degradation reactions, and subsequently the method always requires very large quantities of the solutions to be-treated. However, this method cannot be applied to the preparation of all alkylhydrazines and especially not for the preparation of mono-substituted alkylhydrazines. Moreover, treatment of the synthesis solutions requires the extraction of water and then amine, which requires costly operations.

SUMMARY OF THE INVENTION

The inventors have now discovered a novel method of synthesis of monoalkylhydrazines, in particular of allylhydrazine. This method, implemented continuously, is based on a transposition of the Raschig method, and it consists of preparing chloramine by the action of sodium hypochlorite on ammonia at low temperature, then making the chloramine thus produced act on alkylamine in a homogeneous or heterogeneous medium, then recycling the amine and extracting the hydrazine thus formed. The starting amine can be recycled.

DETAILED DESCRIPTION OF THE INVENTION

Figure 1:
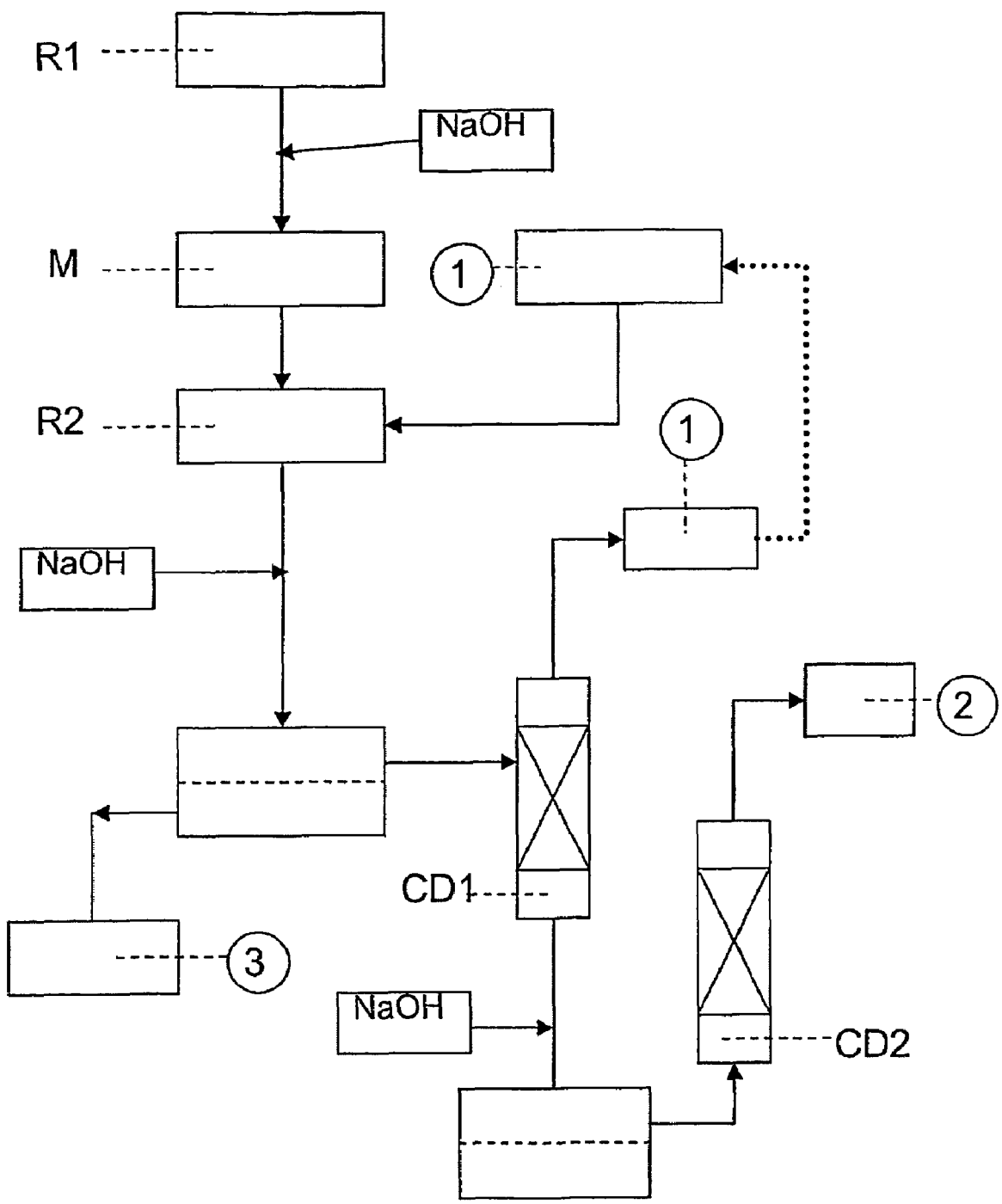
FIG. 1 is a schematic diagram representing one embodiment of the method of the invention.

The present invention makes possible a simple and economic method for obtaining alkylhydrazines.

Thus, the present invention has as an object a continuous method for the synthesis of a monoalkylhydrazine of formula $$NH_2\text{—}NH\text{—}R \qquad (I)$$

in which R represents independently an alkenyl radical at $C_2$-$C_6$, an alkynyl radical at $C_2$-$C_6$, a linear alkyl radical at $C_1$-$C_5$ containing at least one imine function (—C=N—) or a linear or branched alkyl radical at $C_1$-$C_6$ carrying at least one functional group selected from the group comprised of the radicals OH, alkoxy at $C_1$-$C_6$, C=NH, C≡N, phenoxy, COOH, COO-alkyl at $C_1$-$C_6$, phenyl or $NR_3R_4$, $R_3$ and $R_4$ each representing independently an alkyl radical at $C_1$-$C_6$ or forming a ring at $C_2$-$C_6$, wherein it comprises the following successive steps:

a) synthesizing the monoalkylhydrazine of formula I in a suitable reactor while causing to react in an alkaline medium and at a temperature in the range between 25 and 45° C. a monochloramine with an anhydrous amine of formula $NH_2$—R (II), R having the same significance as for formula I; then b) demixing the solution obtained following step a in an organic phase and an aqueous phase by the addition of anhydrous sodium hydroxide under cooling so that the temperature of the demixing medium does not exceed the boiling points of the compounds; and c) isolating from the organic phase thus obtained the monoalkylhydrazine of formula I.

During step a, the monochloramine and the anhydrous amine of formula II are advantageously introduced simultaneously.

The synthesis of the monoalkylhydrazine of formula I in step a is carried out in a homogeneous medium or a heterogeneous medium in an appropriate reactor, which is advantageously a stirred tubular reactor. The tubular reactor makes it possible to avoid contact between the nascent monoalkylhydrazine and the monochloramine and thus it makes it possible to avoid an oxidation-reduction reaction between these two reagents. The reaction front moves along the tube and the monoalkylhydrazine no longer remains in contact with the monochloramine injected at the base of the reactor.

According to an advantageous variant of the invention, the concentration in hydroxyl ions in the reaction medium of step a is in the range between 0.3 and 0.8 mol/l.

According to an advantageous variant of the invention, in step a, the anhydrous amine/monochloramine molar ratio of formula II is in the range between 18 and 30, inclusive. The reaction time is variable and depends on the temperature at which the reaction is carried out and on the concentration ratios of the reagents. For example, in the case of the synthesis of monoallylhydrazine, in the range of concentration ratios given and at 25° C., the reaction time is on the order of 2 to 10 minutes.

According to an advantageous variant of the invention, before step a, the monochloramine is alkalized in a mixer by the addition of a sodium hydroxide solution in such a way that the weight concentration in sodium hydroxide in the mixer is in the range between 2% and 6%. The mixer is advantageously maintained at a temperature in the range between −10 and 5° C.

Thus, according to this variant of the invention, the reaction of the monochloramine with the anhydrous amine of formula II is carried out in the presence of an aqueous sodium hydroxide solution at a temperature in the range between 25 and 45° C. When step a comes out of the reactor, that is to say, at the end of the reaction, the concentration in sodium hydroxide is less than 0.3 mol/l. The concentration in soda must not be too high because if it is, the reaction mixture risks demixing by salting out. In the event of salting out, it would then be necessary to use a stirred plug-flow reactor.

During the monoalkylhydrazine synthesis reaction, hydrochloric acid is also formed. The alkalization of the monochloramine, that is to say, the addition of a strong base such as soda, makes it possible to neutralize the acid formed, in order to avoid any local protonation of the amine at the moment of mixing and thus to avoid the formation of a substituted monochloramine, which could cause the formation of di-or tri-substituted alkylhydrazines. The quantity of the strong base added must be sufficient to neutralize all of the acid formed. Moreover, the speed of the formation of the hydrazine increases with the alkalinity of the medium, which is not the case for degradation reactions, such as, for example, the oxidation of the nascent hydrazine by the chloramine.

The monochloramine, advantageously alkalized, and the anhydrous amine of formula II are advantageously introduced into the reactor simultaneously. The flow rates of the addition of the anhydrous amine of formula II and the monochloramine are such that the molar concentration ratio of the heterocyclic amine to the monochloramine is advantageously in the range between 18 and 30, inclusive. In the case of the synthesis of monoallylhydrazine, the synthesis reaction is carried out in a homogeneous medium.

During step b, the quantity of anhydrous sodium hydroxide added is advantageously such that the weight concentration in sodium hydroxide is in the range between 10% and 35%, preferably 30%. Under these conditions, the medium demixes into two phases, one of which, the light phase (organic phase), concentrates the near totality of the organic molecules, in particular the monoalkylhydrazine and the initial amine. This treatment with sodium hydroxide makes it possible by demixing to eliminate at least 70% to 80% by weight, according to the organic character (number of carbon atoms) of the amine and of the monoalkylhydrazine, advantageously approximately 85% by weight, of the water present in the reaction medium and to extract the ammonia formed with salts in the lower phase (aqueous phase). The water content decreases with the number of carbon atoms, and, conversely, increases if hydrophilic functional groups are present.

In the case of the synthesis of allylhydrazine, for example, the temperature of the demixing medium of step b must not exceed 80° C.

Step c advantageously comprises the following successive steps:

i) isolating the unreacted anhydrous amine of formula II and a concentrated solution of the monoalkylhydrazine of formula I by distillation of the organic phase obtained following step b; then ii) if necessary, purifying the aforesaid concentrated solution of the monoalkylhydrazine of formula I.

The distillation, advantageously carried out at atmospheric pressure, makes it possible to recover at the head of the column the totality of the unreacted initial anhydrous amine of formula II at a distillation temperature equal to or slightly above the boiling point of the aforesaid amine without leading to the formation of the monoalkylhydrazine which has a higher boiling point.

The aforesaid amine recovered following step i is advantageously reinjected into the reactor of step a. The aforesaid amine can be reinjected directly, without additional treatment, into the reactor of step a where the monoalkylhydrazine is formed. The concentrated solution of the monoalkylhydrazine of formula I can be purified, if necessary, advantageously by distillation, which can be carried out at atmospheric pressure. This distillation, called final correction, makes it possible to obtain at the head of the column a concentration higher than 95%, advantageously higher than 99%, in monoalkylhydrazine. The aforesaid distillation is possibly preceded by a step of demixing in an organic phase and an aqueous phase by the addition of anhydrous sodium hydroxide in such a way that the weight concentration in sodium hydroxide is in the range between 30% and 50%. This demixing step makes it possible to eliminate the water possibly still present in the concentrated monoalkylhydrazine solution obtained following step i.

The monochloramine introduced in step a is advantageously prepared according to a method comprising the following successive steps:

α) preparing an aqueous sodium hypochlorite solution having a chlorometric degree in the range between 36° and 100°, possibly by the dilution of a hypochlorite solution having a chlorometric degree in the range between 100° and 120°; then β) reacting a solution of ammonium hydroxide and of ammonium chloride with the aqueous sodium hypochlorite solution obtained following step α, in a slightly alkaline medium, at a temperature in the range between −15 and −7° C., in order to form the aforesaid monochloramine.

Within the context of the present invention, the expression "slightly alkaline medium" is understood to mean a medium whose pH value is approximately 10±1.

The molar ratio of the ammonium hydroxide and ammonium chloride solution to the aqueous sodium hypochlorite solution advantageously lies between 2.5 and 3, inclusive.

The molar ratio of the ammonium chloride to the ammonium hydroxide advantageously lies between 0.1 and 1.75, inclusive, more advantageously it is approximately 0.65.

If the chlorinated reagent used in step α is obtained by the dilution of a 100-120° chlorometric high-concentration hypochlorite solution, this dilution presents the advantage of decreasing the sodium chloride content by 40%. This treatment, favorable for the environment, allows the bleach solution to be cooled to −15° C. without the risk of crystallization.

The method developed, which is the object of the present discovery, makes it possible to obtain a perfect selectivity at the level of the monoalkylhydrazine without the presence of its di- and tri-substituted forms, which is one of the major originalities compared to the treatments that use alkylation. It can be considered that the method of synthesis according to the invention never leads to di- or tri-substituted products. Indeed, the non-substituted amine reagent, the monochloramine to be specific, gives up its $NH_2$— group to the amine of formula II by SN2 nucleophilic substitution. The resulting mono-substituted alkylhydrazine will thus retain the same degree of substitution as the precursor amine. This method, which is simple to implement, avoids the various previous complex treatments for isolating the monoalkylhydrazine in the presence of the $H_2O$—$N_2H_4$ mixture.

The method of the present invention thus makes possible not only the continuous synthesis of monoalkylhydrazine, without the formation of any toxic intermediate, but it also makes it possible to obtain the aforesaid hydrazine at a relatively low cost.

The example gives, on a purely non-limiting basis, a detailed description of the implementation of the method of the invention, a method whose schematic diagram is represented FIG. 1.

Significance of the Abbreviations Used:
R1: Reactor 1
M: Mixer
R2: Reactor 2
CD1: Distilling column no. 1
CD2: Distilling column no. 2
1: Anhydrous allylamine
2: Allylhydrazine
3: Water+$NH_3$+NaCl+NaOH solution

EXAMPLE

Continuous Preparation of the Monoallylhydrazine

All of the quantities indicated correspond to a unit system and are in relation to a liter of hypochlorite injected.

One liter of a sodium hypochlorite solution elaborated by the dilution of 50% of a high-concentration hypochlorite solution (100-120° chlorometric, which is after dilution [NaOCl]=2.14 mol/l and [NaCl]=0.85 mol/l) and a liter of a solution having an ammonia concentration of 3.60 mol/l and an ammonium chloride concentration of 2.38 mol/l are each introduced continuously into a stirred reactor (R1) at a rate of 5 ml/min (which is 6 g/min of the 480 chlorometric hypochlorite solution and 5.05 g/min of the $NH_3$+$NH_4Cl$ ammonia mixture).

The temperature within the reactor is maintained in the range between −8 and −11° C., and the pH of the reaction is approximately 10. Upon removal from R1, a monochloramine solution of a concentration greater than 1 mol/l is obtained, which corresponds to a yield near 100% with respect to the sodium hypochlorite.

Upon removal from R1, the monochloramine solution obtained above (2 liters) is alkalized by the continuous introduction of a concentrated solution of sodium hydroxide (0.39 liter at 30% by weight) into a double-wall mixer (M) maintained at a low temperature in the range between −9 and −11° C. Homogenization is ensured by a magnetic drive.

The synthesis of the monoallylhydrazine is carried out by means of a stirred tubular reactor (R2). The alkalized monochloramine (2.39 liters), arising from the container of the mixer M, and the anhydrous allylamine (3.25 liters, which is 2.46 kg due to its density of 0.760) are introduced simultaneously at the base of the reactor by means of metering pumps. The flow rate of the anhydrous allylhydrazine is 16.46 ml/min and a part of the reaction is carried out in a homogeneous medium at 35° C. The final concentration in NaOH upon exit from R2 is 0.3 mol/l.

This present method is characterized such that the sodium hydroxide is added to the homogeneous reaction liquor (5.6 kg) according to a weight concentration preferably in the range between 30% and 40% and under cooling so that the temperature does not exceed 45° C. Under these conditions, two phases are obtained, one of which, the light phase (approximately 2 kg), contains the totality of the organics, that is to say, the monoallylhydrazine and the excess allylamine. This treatment thus makes it possible to eliminate between 80% and 85% by weight of the water present in the synthesis solutions.

Obtaining the monoallylhydrazine then requires two successive steps:
  Recovery of the unreacted allylamine by the distillation of the phase at atmospheric pressure. Approximately 1.7 kg of anhydrous amine is recovered at a temperature of 52° C. (distilling column CD1), which is reinjected without treatment into the reactor R2.
  Purification of the solution obtained in the base of the column (distilling column CD2) after separation by the addition of sodium hydroxide (40% to 50%). Before purification, the light phase has a concentration in monoallylhydrazine of at least 95%.

After purification, the monoallylhydrazine having a degree of purity greater, than 99% is obtained. The yield in the monoallylhydrazine with respect to the allylamine consumed is greater than 80%.

The invention claimed is:

1. A method for the continuous synthesis of a monoalkylhydrazine of formula $$NH_2—NH—R \qquad (I)$$

in which R is selected from the group consisting of $C_2$-$C_6$ alkenyl radical, $C_2$-$C_6$ alkynyl radical, $C_1$-$C_5$ linear alkyl radical containing at least one imine function (—C≡N—), and linear or branched $C_1$-$C_6$ alkyl radical carrying at least one functional group selected from the group consisting of OH, $C_1$-$C_6$ alkoxy, C=NH, C≡N, phenoxy, COOH, COO—($C_1$-$C_6$ alkyl), phenyl or $NR_3R_4$, with $R_3$ and $R_4$ each representing independently a $C_1$-$C_6$ alkyl radical or forming a $C_2$-$C_6$ ring, wherein the method comprises the following successive steps:

(a) synthesizing the monoalkylhydrazine of formula I in a suitable reactor while causing to react in an alkaline medium and at a temperature in the range between 25 and 45° C. a monochloramine with an anhydrous amine of formula $$NH_2—R \qquad (II)$$

R having the same significance as for formula I; then (b) demixing the solution obtained following step (a) in an organic phase and an aqueous phase by the addition of anhydrous sodium hydroxide under cooling so that the temperature of the demixing medium does not exceed the boiling points of the compounds; and (c) isolating from the organic phase thus obtained the monoalkylhydrazine of formula I.

2. The method according to claim 1, wherein, in step (a), the formula II anhydrous amine/monochloramine molar ratio is in the range between 18 and 30.

3. The method according to claim 1, wherein the reactor used in step (a) is a stirred tubular reactor.

4. The method according to claim 1, wherein before step (a) the monochloramine is alkalized in a mixer by the addition of a solution of sodium hydroxide in such a way that the weight concentration of sodium hydroxide is in the range between 2% and 6%.

5. The method according to claim 4, wherein the mixer is maintained at a temperature in the range between −10 and 5° C.

6. The method according to claim 1, wherein the quantity of the anhydrous sodium hydroxide added during step (b) is such that the weight concentration of sodium hydroxide is in the range between 10% and 35%.

7. The method according to claim 1, wherein step (c) comprises:

(i) isolating the unreacted anhydrous amine of formula II and a concentrated solution of the monoalkylhydrazine of formula I by distillation of the organic phase obtained following step (b).

8. The method according to claim 7, wherein step (c) further comprises following step (i), a step (ii) of purifying said concentrated solution of the monoalkylhydrazine of formula I.

9. The method according to claim 7, wherein said unreacted anhydrous amine of formula II is reinjected into the reactor of step (a).

10. The method according to claim 8, wherein the concentrated monoalkylhydrazine solution of formula I is purified by distillation.

11. The method according to claim 10, wherein the distillation is preceded by a step of demixing into an organic phase and an aqueous phase by the addition of anhydrous sodium hydroxide in such a way that the weight concentration of sodium hydroxide is in the range between 30% and 50%.

12. The method according to claim 1, wherein the monochloramine is prepared according to a method comprised of the following successive steps:

α) preparing an aqueous sodium hypochlorite solution having a chlorometric degree in the range between 36° and 100°; and β) reacting a solution of ammonium hydroxide and of ammonium chloride with the aqueous sodium hypochlorite solution obtained following step (α), in a slightly alkaline medium, at a temperature in the range between −15 and −7° C., in order to form the monochloramine.

13. The method according to claim 12, wherein said aqueous sodium hypochlorite solution is prepared by the dilution of a hypochlorite solution having a chlorometric degree in the range between 100° and 120°.

14. The method according to claim 12, wherein the molar ratio of the ammonium hydroxide and ammonium chloride solution to the aqueous sodium hypochlorite solution is between 2.5 and 3.

15. The method according to claim 14, wherein the molar ratio of the ammonium chloride to the ammonium hydroxide is between 0.1 and 1.75.

16. The method according to claim 14, wherein the molar ratio of the ammonium chloride to the ammonium hydroxide is 0.65.

* * * * *